United States Patent [19]

Cottingham

[11] Patent Number: 4,775,515

[45] Date of Patent: * Oct. 4, 1988

[54] AGGLUTINOGRAPHIC SLIDE

[76] Inventor: Hugh V. Cottingham, 49 Mountain Ave., Caldwell, N.J. 07006

[*] Notice: The portion of the term of this patent subsequent to Jun. 24, 2003 has been disclaimed.

[21] Appl. No.: 932,067

[22] Filed: Nov. 18, 1986

[51] Int. Cl.<sup>4</sup> .................. G01N 1/18; G01N 21/03; G01N 33/50
[52] U.S. Cl. ........................ 422/73; 422/58; 422/101; 422/102; 436/46; 436/165; 436/177; 436/178; 356/244; 356/246; 350/534; 350/536
[58] Field of Search .......... 422/55, 58, 72, 73, 422/101, 102; 436/45, 46, 165, 177, 178; 356/244, 246; 350/534, 536; 73/864.02, 864.72

[56] References Cited

U.S. PATENT DOCUMENTS

| 3,799,742 | 3/1974 | Coleman | 422/102 |
| 4,426,451 | 1/1984 | Columbus | 422/58 |
| 4,557,600 | 12/1985 | Klose et al. | 436/45 |
| 4,596,695 | 6/1986 | Cottingham | 422/58 |

Primary Examiner—Barry S. Richman
Assistant Examiner—Lynn M. Kummert
Attorney, Agent, or Firm—Blum Kaplan

[57] ABSTRACT

An agglutinographic slide for immunochemical liquid agglutionation particle reagents has a first panel and a second panel. The second panel is spaced a predetermined distance from the first panel. The slide has an entrance end and a viewing end. A channel is positioned between the first and second panels so that liquid agglutination particle reagents are transported from the entrance end to the viewing end. The channel has a length greater than the length of the slide to allow control of flow and enhance the viewability of the reaction.

18 Claims, 2 Drawing Sheets

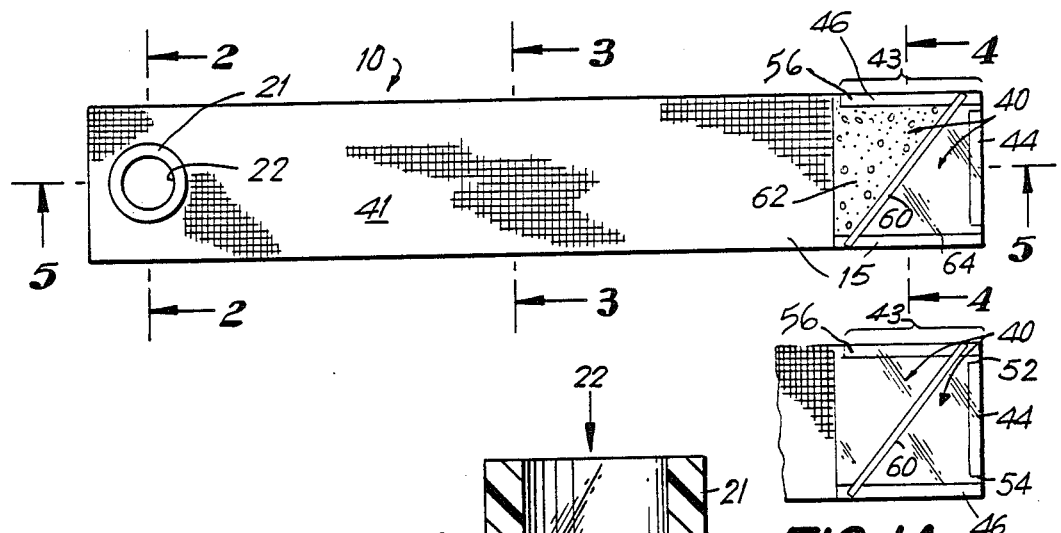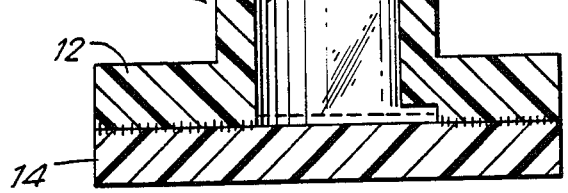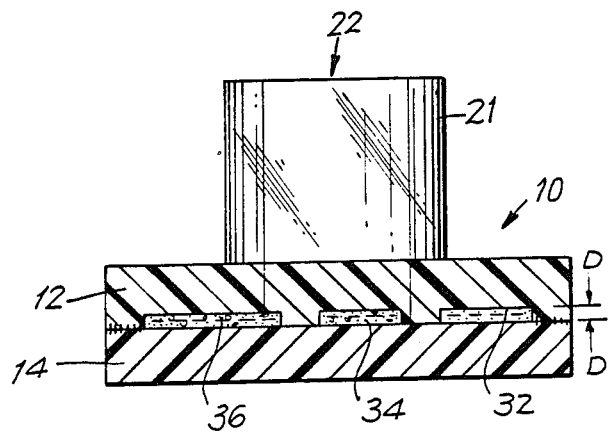

AGGLUTINOGRAPHIC SLIDE

BACKGROUND OF THE INVENTION

This invention is generally directed to an improved chamber configuration for reacting immunochemical particles, and in particular to an agglutinographic reaction slide chamber which improves the visual response of an immunochemical reaction occurring therein. The process by which a stable, high contrast visual record of an immunochemical particle agglutination reaction occurs, without the necessity of shaking, rocking or otherwise adding external kinetic energy thereto, is referred to herein as "agglutinography" or an "agglutinographic reaction."

In U.S. Pat. No. 4,596,695, issued June 24, 1986 to the inventor of the instant invention, the slide chamber described therein is configured to intrinsically produce agglutinations for optical detection of a reaction when a test sample is combined with a reagent. Although the slide chamber described in U.S. Pat. No. 4,596,695 intrinscially produces detectable agglutinographic reactions, the slide chamber described therein is less than completely satisfactory in several respects. In particular, manufacturing constraints, the importance of maintaining the stability of each reaction, obtaining a clearly discernible visual response using highly sensitive reagents and facilitating visual differentiation of the presence or absence of a reaction are each benefits which, if obtained, will overcome disadvantages of the test chamber described in U.S. Pat. No. 4,596,695.

Accordingly, a test chamber that is easy to manufacture, produces systematic, stable and highly reproducible tests on highly sensitive agglutinographic reagents, and permits the absence or presence of a reaction to be easily discerned is provided by the instant invention.

SUMMARY OF THE INVENTION

Generally speaking, in accordance with the instant invention, an agglutinographic test chamber for controlling an immunochemical liquid agglutination particle reaction is provided. The test chamber includes a first panel and a second panel. The second panel is at least partly co-extensive with the first panel and is spaced apart a pre-determined distance from the first panel to define a chamber. An entrance opening for the chamber is provided for receiving liquid sample. At least a portion of one of the panels is transparent to allow optical detection of agglutinations when an agglutination reaction occurs in the chamber. A channel structure is defined between the panels, the channel having a length greater than the length of the chamber defined by the panels so that the time of the reaction is increased and thereby enhancing the visual response of the reaction by permitting larger agglutinations to occur.

In a preferred embodiment, vent holes are provided in the chamber to allow air pushed ahead of the liquid to escape and reduce evaporation. A differentiation window is defined by the transparent portion for facilitating differentiation between a reaction and a non-reaction.

Accordingly, it is an object of the instant invention to provide an improved agglutinographic test chamber.

A further object of the instant invention is to provide a chamber configuration that by its configuration creates larger and hence easier to view agglutinations.

Another object of the instant invention is to create a chamber having a length that is greater than the length of the panels defining the chamber.

A further object of the instant invention is to provide a test chamber slide configuration that is easy to manufacture.

Another object of the instant invention is to provide an agglutinographics slide which allows the user to easily optically differentiate a reaction from a non-reaction.

Still other objects and advantages of the invention will in part be obvious and in part will be apparent from the specification.

The invention accordingly, comprises the features of construction, combination of elements, and arrangements of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a top plan view of an agglutinographic reaction chamber constructed in accordance with a preferred embodiment of the invention when agglutinations occur;

FIG. 1A is a partial top plan view of the viewing chamber in the chamber depicted in FIG. 1 when no agglutinations are caused by the reaction;

FIG. 2 is a sectional view taken along line 2—2 of FIG. 1;

FIG. 3 is a sectional view taken along line 3—3 of FIG. 1;

DETAILED DESCRIPTION OF THE PREFERRED EMBODIMENTS

Figure 4:
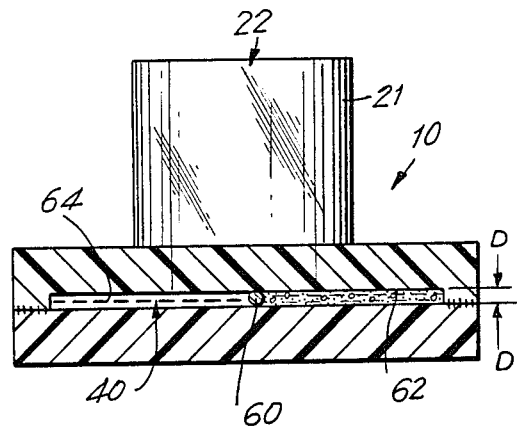
FIG. 4 is a sectional view taken along line 4—4 of FIG. 1.
Figure 5:
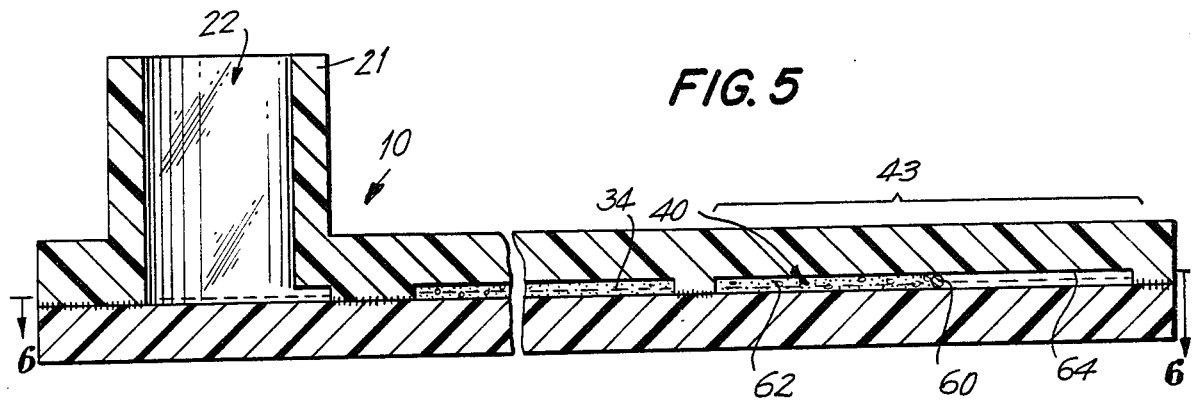
FIG. 5 is a partial sectional view taken along line 5—5 of FIG. 1.
Figure 6:
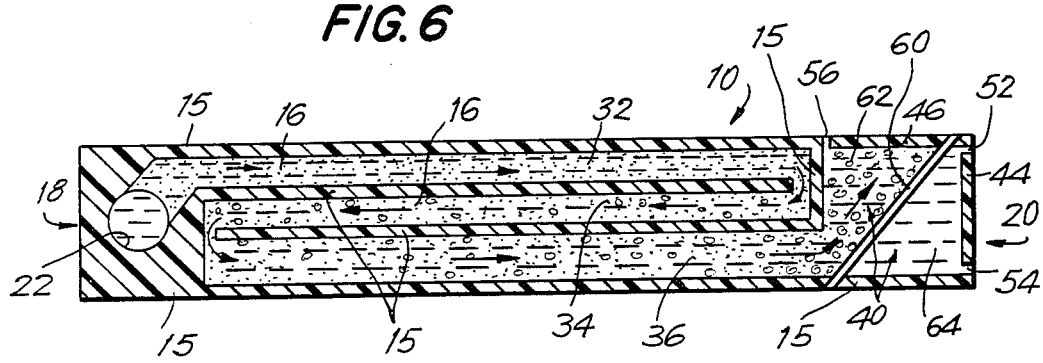
FIG. 6 is a sectional view taken along line 6—6 of FIG. 5.

Reference is first made to the drawings, wherein an agglutinographic reaction chamber, generally indicated as 10, constructed in accordance with the instant invention is depicted. Chamber 10 is comprised of an upper panel 12 spaced apart from a lower panel 14 by narrow gap D—D. Although either panels 12 and 14 or both panels can be formed of any wettable material, such as glass or coated materials, in an exemplary embodiment of the instant invention, the panels are formed of an injection molded acrylic resin to facilitate assembly thereof. As is particularly illustrated in FIG. 6, top panel 12 is molded to define a plurality of integrally formed spacers, generally identified as 15, which spacers define a channel 16.

In an exemplary embodiment, chamber 10 includes an entrance end, generally indicated at 18, and a viewing end generally indicated at 20. At the entrance end, an entrance opening 22 is defined by a cylindrical wall 21 projecting from panel 12. Opening 22 is open to channel 16. Spacers 15 perform the dual function of separating panel 12 from panel 14 and forming channel 16. Channel 16 is continuous yet nonlinear, and is characterized by three channel sections 32, 34 and 36. Channel section 32 cooperates with entrance opening 22 at one end and channel section 34 at the other end. Channel section 34 cooperates with channel section 32 at its one end and channel section 36 at its other end, and channel section 36 cooperates with channel section 34 at its one end and viewing chamber 40 at its other end so that a continuous channel is defined by entrance opening 22, first channel section 32, channel section 34, channel section 36 and viewing chamber 40.

Immunochemical particle reagents in a liquid are introduced into channel 16 through opening 22. Specifically, a volume of a liquid sample to be tested is introduced into opening 22 and drawn into channel 16 by capillary action causing the test sample to be drawn through the entire length of channel 16 and ultimately introduced in the viewing chamber 40. When an agglutination reaction occurs, the agglutinations are visible at the viewing end 20. The manner in which the panels are spaced apart to define a capillary action and cause an agglutination reaction liquid test sample to be drawn through the reaction chamber is described in U.S. Pat. No. 4,596,695, which patent is incorporated by reference as if fully set forth herein.

Channel section 36 has a width that is greater than the width of either channel section 32 or 34. This allows for graded rates of flow when a test sample passes through channel 16. Specifically, a liquid test sample will flow faster through channel sections 32 and 34 causing a better diffusing of the reagents. The rate of flow of the sample-reagent mixture is slower in channel 36 encouraging the production of larger agglutinations as the sample/reagent mixture is introduced into viewing chamber 40. Two separate characteristics of channel 16 are obtained by the configuration illustrated in the drawings. The first characteristic is the manner in which channel sections 32, 34 and 36 define a continuous channel that has a length that exceeds the length of the panels. The second characteristic is the graded rates of flow that occur by reason of the distinct geometry of each of the channel sections. Specifically, the channel sections in combination with the length generate a non-linear flow rate. This nonlinear flow rate has been used to create the largest possible agglutinations. Specifically, in the sections of the channel closer to the window chamber, the flow is slower yielding larger agglutinations that would otherwise not form or would be broken up by a higher flow rate. However, additionally, channel section 36 is wider than sections 34 and 32 in order to obtain higher diffusions of test samples and reagents closer to the entrance opening at the early part of the reaction and to optimize the size of the agglutinations formed near the window chamber to enhance the viewability of such agglutinations. This enables slide 10 to make more efficient use of space as well as extending the time of the agglutinographic reaction. By increasing the time of the reaction, the visual response of the reaction occurring in channel 16 is enhanced, particularly when highly sensitive agglutination reagents are utilized.

In order to permit unambiguous viewing of the reaction or absence thereof, a substantial portion of the surface area 41 of top panel 12 and all or part of bottom panel 14 are rendered opaque by etching, roughening the surface of the slide or by the application of an opaque layer such as tape, paint, etc. In an exemplary embodiment, the only surface that remains transparent in the area 43 in the top panel that is coextensive with the viewing chamber 40. As aforenoted, viewing chamber 40 communicates with channel section 36 so that the sample agglutination reagent mixture flows into chamber 40.

Spacers 44 and 46 are positioned at the viewing end and are spaced apart from spacers 15 and from each other to define vent holes 52, 54, 56 communicating with viewing chamber 40. Vent holes 52, 54 and 56 prevent blockage of the flow of the reagent mixture due to air trapped within the lengthwise extent of channel 16 and chamber 40 disposed in the slide 10 by providing an escape for the air pushed ahead of the reagent mixture. Vent holes 52, 54 and 56 also act to reduce random evaporation that would occur if viewing end 20 were completely open and, as a result, provides a systematic manner in which to control the end point of the reaction. Furthermore, by providing vent holes in a viewing chamber, as opposed to providing an open viewing area, the likelihood of the test sample running out a large opening during handling is decreased.

In a preferred embodiment of the invention, as depicted in FIG. 1, an agglutinographic slide 10 is constructed as follows. Upper panel 12 and lower panel 14 are acrylic. Panel 12 and panel 14 are 3.00 inches × 0.525 inches. Viewing chamber 32 is 0.500 inches × 0.525 inches and each vent hole 52, 54, 56 is on the order of 0.025 inches wide. Channel sections 32 and 34 have a width of 0.100 inches and lengths of approximately 2.020 inches. Channel section 36 has a width of 0.125 inches and a length that is approximately 2.020 inches. Spacers 15 have a height of 0.0065 inches and a width of 0.050 inches. Entrance opening 22 has a diameter of 0.3 inches.

As noted above, in an exemplary embodiment, spacers 15 define a gap between panels 12 and 14 of 0.0065 inches. It is noted that each of the dimensions detailed above, including the gap, are provided by way of example. However, if the gap is smaller, the capillary force of the chamber and the resistance to flow increases. If the gap increases, the capillary flow of the chamber is reduced and the resistance to flow is reduced. Thus, by varying the gap between the first and second panels, the speed of the liquid flow can be varied thus affecting the reaction. Accordingly, a gap on the order of 0.001 inches to 0.020 inches can be utilized when acrylic resin panels are utilized.

A liquid permeable agglutination filter 60 is affixed diagonally across viewing chamber 40. Agglutination filter 60 acts as a filter and permits the solution and unagglutinated monomeric latex reagent to pass across filter 60 while preventing agglutinations from passing therethrough. This allows users not familiar with agglutinations, per se, to easily read the results of any tests by providing visually dissimilar halves 62,64 within chamber 40 when large agglutinations are produced. In a preferred embodiment, filter 60 is made of a polyester cotton filter. It is noted however that the slide chamber of the instant invention permits agglutination reactions to be easily read with or without filter 60. However, filter 60 permits reading of the viewing chamber to be further facilitated.

A direct test can be performed by applying a urine sample containing HCG and agglutination reagent to the test chamber. Agglutinations of latex will occur when certain HCG is present in the urine sample. If, however, no HCG is present in the sample no agglutination will occur. Chamber 10 may also be used for indirect testing in which the latex reagents contain the hormones being tested for and an antibody solution and a urine sample. In such case, if the sample also contains a hormone, no reaction will occur and if agglutinations do occur then the test is negative.

Test samples and reagents may be introduced to the test chamber in a variety of ways. In a preferred embodiment, reagents are dried in channel section 32 at entrance opening 22. Next, a test sample is pipetted into entrance opening 22. The presence of the liquid sample causes the dried reagents to immediately dissolve. Next, the capillary action causes the liquid sample to pass through channel section 32 and to begin diffusing with the reagents. Any manner for drying may be used, but freeze drying is preferred. In another embodiment, reagents may be freeze dried outside of test chamber 10 and placed in opening 22 so that when the sample is added to chamber 10, the sample liquifies the reagent and they both flow through the chamber, or the reagent and test sample may be combined in liquid form outside of the chamber and then pipetted into the entrance opening 22.

Capillary action is a function of surface forces, therefore the length of time for agglutinations to occur within channel 16 may be lengthened or shortened by treating the surface of slide 10. For example, the period of time of liquid flow in an acrylic chamber may be reduced by treating the acrylic surfaces with monohydric alcohol such as isopropyl alcohol.

Accordingly, by providing an agglutinographic chamber with a channel having differently sized channel sections, it is possible to control the rate of agglutination as well as where the agglutinations will occur. By providing vent holes, evaporation of the sample may also be reduced. Also, by providing a liquid permeable filter the ease with which a user may detect agglutinations is greatly enhanced.

Thus, the instant invention is characterized by an agglutinographic chamber having an elongated channel that is of greater length than the panels forming the chamber. By lengthening the channel, larger agglutinations that are easier to view are obtained. Furthermore, by utilizing a viewing chamber having vent holes and a filter, a more reproducible and easier to view reaction is obtained. Finally, by incorporating each of the features aforenoted, the agglutinographic chamber of the instant invention can be easily manufactured using conventional injection molding techniques and ultrasonic welding and, if appropriate, drying of the reagents to complete the product.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is understood that the following claims are intended to cover all of the generic and specific features of the invention herein described and all statements of the scope of the invention which, as a matter of language, might be said to fall therebetween.

What is claimed is:

1. In an agglutinographic slide for reacting immuno-chemical liquid agglutination particle reagents comprising an immuno-chemical liquid agglutination particle reagent, first panel means of a predetermined length and second panel means of a predetermined length spaced apart from said first panel means a predetermined distance of 0.1 to 500 $\mu$ and substantially disposed coextensively with said first panel means to define a capillary channel means therebetween and for causing an agglutination reaction to intrinsically occur within the said channel means, the improvement comprising at least one of said panel means defining an entrance opening, said agglutination particle reagent being disposed in proximity to said entrance opening and said first panel means and second panel means defining a viewing chamber, said channel means extending from said entrance opening to said viewing chamber, said channel means having a length that is greater than the predetermined length of one of said first panel means and said second panel means.

2. The agglutinographic slide, as claimed in claim 1, wherein said channel means includes a width along the length thereof, said width being selectively graded to control the rate of flow of said liquid and reagent through said channel means.

3. The agglutinographic slide, as claimed in claim 1, further comprising a venting means in connection with said viewing chamber for allowing the escape of air from said slide as said liquid travels towards said viewing chamber and configured to minimize evaporation at the viewing chamber.

4. The agglutinographic slide, as claimed in claim 1, wherein said channel means comprises at least a first channel section and a second channel section, said first channel section and said second channel section being configured in fluid communication and disposed with respect to each other to permit reagents to flow from said entrance opening through said first channel section to said second channel section and into said viewing chamber.

5. The agglutinographic slide, as claimed in claim 4, wherein the first channel section has a predetermined width and the second channel section has a predetermined width, the width of said second channel section is wider than the width of said first channel section in order to slow down the rate of flow of liquid reagent in said second channel section.

6. The agglutinographic slide, as claimed in claim 1, and including agglutination differentiating means disposed in said viewing chamber for differentiating formed agglutinations from non-agglutinations in said reagents so that the difference therebetween is easily viewed.

7. The agglutinographic slide, as claimed in claim 6, wherein said agglutination differentiating means includes a liquid permeable filter, said filter being positioned within said viewing chamber so that said filter is adapted to prevent agglutinations from passing from one side of the filter to an opposite side of said filter.

8. The agglutinographic slide, as claimed in claim 1, and including at least one of said first panel means and said second panel means includes a coating to control the flow rate of said reagent in said channel means.

9. The agglutinographic slide, as claimed in claim 8, wherein said coating is monohydric alcohol.

10. In an agglutinographic test slide for immunochemical liquid agglutination particle reagents comprising in combination an immuno-chemical liquid agglutination particle reagent, a first panel having a predetermined length, a second panel having a predetermined length, said second panel being spaced a predetermined distance of 0.1 to 500 $\mu$ from said first panel to define a capillary channel means therebetween of a predetermined length, the improvement comprising an entrance opening for introducing liquid reagents to said channel means, said agglutination particle reagent being disposed in proximity to said entrance opening, said channel means having a length that exceeds the length of said first panel for transmitting said liquid agglutination particle reagent from said entrance opening through said channel means, said channel means including first and second channel sections configured to allow said liquid to flow from said first channel section to said second channel section, said first channel section having a width, said second channel section having a width greater than the width of said first channel section for reducing the rate of capillary flow of the reagents to enhance the size of the agglutinations thereby enhancing the viewability thereof.

11. An agglutinographic slide, as claimed in claim 10, wherein said channel means is defined by spacers disposed between said first and second panels, said spacers being integrally formed with one of said first and second panels.

12. An agglutination slide, as claimed in claim 10, wherein said second channel section includes an exit end, and a viewing chamber disposed at the end of said second channel section, said first panel being transparent in the portion thereof that is coextensive with said viewing chamber.

13. An agglutinographic slide, as claimed in claim 12, wherein said viewing chamber vent holes in communication therewith for allowing air to escape from said channel means when reagents flow from said entrance opening to said viewing chamber.

14. An agglutinographic slide, as claimed in claim 12, and including filter means disposed in said viewing chamber, said filter means being positioned and arranged to prevent agglutinations that are formed from passing therethrough, so that a viewing chamber that is capable of differentiating between agglutinations and non-agglutinations is provided.

15. In an agglutinographic test slide for immuno-chemical liquid agglutination particle reagents comprising in combination an immuno-chemical liquid agglutination particle reagent, a first panel, a second panel, said second panel being spaced a predetermined distance of 0.1 to 500 $\mu$ from said first panel to define a capillary channel means therebetween of a predetermined length, the improvement comprising an entrance opening for introducing liquid reagents to said channel means, said agglutination particle reagent being disposed in proximity to said entrance opening, said capillary channel means including a viewing chamber so that said liquid reagents are transmitted from said entrance opening through the length of said channel means to said viewing chamber, said channel means and viewing chamber being configured to optimize the size of the agglutinations found in the viewing chamber to enhance the viewability presented at the viewing chamber and said panel is transparent at least in the portion thereof that is coextensive with said viewing chamber the remaining portion of said channel means being nontransparent.

16. An agglutinographic slide, as claimed in claim 15, wherein said viewing chamber includes vent holes for allowing air to escape from said channel means when reagents flow from said entrance opening to said viewing chamber.

17. An agglutinographic slide, as claimed in claim 16, and including filter means disposed in said viewing chamber, dividing said viewing chamber into a first portion and a second portion, said filter means preventing agglutinations that are formed from passing therethrough, so that a viewing chamber that is capable of differentiating between agglutinations and non-agglutinations is provided.

18. An agglutinographic slide, as claimed in claim 16, wherein agglutination reagents are dried in said channel means at said opening and are adapted to be dissolved upon introduction of a liquid test sample into said channel means.

* * * * *